(12) United States Patent
Stevens et al.

(10) Patent No.: US 10,081,864 B2
(45) Date of Patent: Sep. 25, 2018

(54) METHOD AND APPARATUS FOR TREATING CONTAINERS

(75) Inventors: Ronald Stevens, San Ramon, CA (US);
Gabriel Ormonde, Lathrop, CA (US);
James Mitchener, Danville, CA (US)

(73) Assignee: KAIATECH, INC, Danville, CA (US)

( * ) Notice: Subject to any disclaimer, the term of this patent is extended or adjusted under 35 U.S.C. 154(b) by 1060 days.

(21) Appl. No.: 13/417,226

(22) Filed: Mar. 10, 2012

(65) Prior Publication Data

US 2012/0231182 A1    Sep. 13, 2012

Related U.S. Application Data

(60) Provisional application No. 61/451,578, filed on Mar. 10, 2011.

(51) Int. Cl.
| | |
|---|---|
| *C23C 16/50* | (2006.01) |
| *C23C 16/04* | (2006.01) |
| *A61L 2/14* | (2006.01) |
| *C23C 16/30* | (2006.01) |
| *C23C 16/40* | (2006.01) |
| *C23C 16/509* | (2006.01) |
| *H01J 37/32* | (2006.01) |

(52) U.S. Cl.
CPC .............. *C23C 16/045* (2013.01); *A61L 2/14* (2013.01); *C23C 16/308* (2013.01); *C23C 16/401* (2013.01); *C23C 16/403* (2013.01); *C23C 16/5093* (2013.01); *H01J 37/32082* (2013.01); *H01J 37/32394* (2013.01); *H01J 37/32403* (2013.01); *H01J 37/32431* (2013.01); *H01J 37/32522* (2013.01); *H01J 37/32541* (2013.01); *H01J 37/32568* (2013.01); *H01J 37/32596* (2013.01); *A61L 2202/23* (2013.01)

(58) Field of Classification Search
CPC . C23C 16/045; C23C 14/046; C23C 16/5093; C23C 16/45576; H01J 37/32394; H01J 37/32403; H01J 37/32596
See application file for complete search history.

(56) References Cited

U.S. PATENT DOCUMENTS

| | | | |
|---|---|---|---|
| 4,478,874 | A | 10/1984 | Hahn |
| 5,374,314 | A | 12/1994 | Babacz |
| 5,565,248 | A | 10/1996 | Plester et al. |
| 5,641,559 | A | 6/1997 | Namiki |
| 5,670,224 | A | 9/1997 | Izu et al. |
| 5,704,983 | A | 1/1998 | Thomas et al. |

(Continued)

FOREIGN PATENT DOCUMENTS

WO    WO 2009112053 A1 *    9/2009

OTHER PUBLICATIONS

"Barrier Films: SiOx Barrier Benefits: Future of High-Barrier Packaging Films," Penton Media, Inc., 2008, 4 pages, [Online] [Retrieved on Feb. 28, 2011] Retrieved from the Internet<URL:http://www.printthis.clickability.com/pt/cpt?expire=&title=Barrier+Film.>.

(Continued)

*Primary Examiner* — Aiden Lee
(74) *Attorney, Agent, or Firm* — Budzyn IP Law, LLC

(57) ABSTRACT

An apparatus for treating the interior of containers includes a chamber for holding a container and provides precursor materials via an annulus formed by coaxially arranged electrodes at which plasma is created upon application of voltage and the container is treated.

8 Claims, 17 Drawing Sheets

(56) References Cited

U.S. PATENT DOCUMENTS

| | | | |
|---|---|---|---|
| 5,736,207 | A | 4/1998 | Walther et al. |
| 5,800,620 | A * | 9/1998 | Rudder et al. ............. 118/723 I |
| 5,800,880 | A | 9/1998 | Laurent |
| 5,849,366 | A | 12/1998 | Plester |
| 5,935,391 | A * | 8/1999 | Nakahigashi et al. ... 204/192.12 |
| 6,077,388 | A * | 6/2000 | Freeman ................. H05H 1/24 |
| | | | 118/723 DC |
| 6,112,695 | A | 9/2000 | Felts |
| 6,180,191 | B1 | 1/2001 | Felts |
| 6,276,296 | B1 | 8/2001 | Plester |
| 6,328,805 | B1 | 12/2001 | Rius |
| 6,376,028 | B1 | 4/2002 | Laurent et al. |
| 6,486,593 | B1 | 11/2002 | Wang et al. |
| 6,818,310 | B2 | 11/2004 | Namiki et al. |
| 7,122,234 | B2 | 10/2006 | Olofsson et al. |
| 7,399,500 | B2 | 7/2008 | Bicker et al. |
| 7,488,683 | B2 | 2/2009 | Kobayashi et al. |
| 7,513,953 | B1 | 4/2009 | Felts |
| 7,670,453 | B1 | 3/2010 | Chollet |
| 7,678,430 | B2 | 3/2010 | Rius et al. |
| 7,699,933 | B2 | 4/2010 | Lizenberg et al. |
| 7,847,209 | B2 | 12/2010 | Namiki et al. |
| 7,931,955 | B2 | 4/2011 | Behle et al. |
| 2001/0042510 | A1 | 11/2001 | Plester |
| 2003/0228413 | A1 * | 12/2003 | Ohta ..................... C23C 16/452 |
| | | | 427/162 |
| 2004/0099214 | A1 * | 5/2004 | Hama ................... C23C 16/045 |
| | | | 118/723 E |
| 2005/0247667 | A1 * | 11/2005 | Kim et al. ....................... 216/57 |
| 2006/0062931 | A1 | 3/2006 | Rius et al. |
| 2006/0198965 | A1 * | 9/2006 | Tudhope ............. C23C 16/0245 |
| | | | 427/569 |
| 2008/0087221 | A1 | 4/2008 | Duclos et al. |
| 2008/0121176 | A1 | 5/2008 | Duclos |
| 2008/0206477 | A1 | 8/2008 | Rius |
| 2008/0282980 | A1 | 11/2008 | Rius |
| 2008/0292781 | A1 | 11/2008 | Rius et al. |
| 2009/0061111 | A1 | 3/2009 | Mishima et al. |
| 2009/0133626 | A1 | 5/2009 | Rius et al. |
| 2009/0181185 | A1 * | 7/2009 | Grosse ..................... B05D 1/62 |
| | | | 427/569 |
| 2009/0229521 | A1 | 9/2009 | Rius et al. |
| 2009/0280268 | A1 | 11/2009 | Glukhoy et al. |
| 2010/0000856 | A1 | 1/2010 | Chomel et al. |
| 2010/0007100 | A1 | 1/2010 | Duclos |
| 2010/0034985 | A1 | 2/2010 | Krueger et al. |
| 2010/0096393 | A1 * | 4/2010 | Asahara et al. .............. 220/660 |
| 2010/0112252 | A1 | 5/2010 | Ito et al. |
| 2010/0193461 | A1 | 8/2010 | Boutroy et al. |
| 2010/0206232 | A1 | 8/2010 | Duclos et al. |
| 2011/0101862 | A1 * | 5/2011 | Koo ................. H01J 37/32366 |
| | | | 315/111.21 |

OTHER PUBLICATIONS

Chifen, A., "Plasma Polymerized Biofunctional Multilayers Based on a SiO$_2$-like Adhesion Promoting Film," Apr. 2007, one hundred forty-eight pages.

Creatore, M. et al., "Diagnostics and Insights on PECVD for Gas-barrier Coatings," *Pure Appl. Chem.*, 2002, pp. 407-411, vol. 74, No. 3.

Deilmann, M., "Dissertation: Silicon Oxide Permeation Barrier Coating and Sterilization of PET Bottles by Pulsed Low-Pressure Microwave Plasmas," 2008, one hundred forty-two pages.

Fairfield, C., "Optimization of ION and Electron Properties in IC Packaging Applications: Plasma surface-treatment techniques can improve wire bonding and eliminate substrate delamination," Nordson Corporation, 2000, six pages.

Foggiato, J., "Chemical Vapor Deposition of Silicon Dioxide Films," *Handbook of Thin Film Deposition*, 2001, Chapter 3, pp. 111-150.

Glick, S.H. et al., "Silicon Oxynitride Thin Film Barriers for PV Packaging," 2005 DOE Solar Energy Technologies, Nov. 7-10, 2005, five pages, Denver, Colorado.

Heckman, R. et al., "The Evolution of RF Power Delivery in Plasma Processing," *Advanced Energy*, Feb. 4, 2009, five pages.

Hernandez, R., "Food Packaging Materials, Barrier Properties, and Selection," 1997, Chapter 8.3.9, one page.

Hitchman, M. et al., "New Approaches to Titania and Silica CVD," *The Electrochemical Society Interface*, Summer 2001, pp. 40-45.

Indutnyy, I.Z. et al., "Effect of Chemical and Radiofrequency Plasma Treatment on Photoluminescence of SiO$_x$ Films," *Semiconductor Physics, Quantum Electronics & Optoelectronics*, 2006, pp. 9-13, vol. 9, No. 1.

Jasso, M. et al., "Coating of PET cords at Atmospheric Pressure Plasma Discharge in the Presence of Butadiene/nitrogen Gas Mixtures," *Surface & Coatings Technology*, 2006, pp. 57-62, vol. 201.

Jeng, M. et al., "A Stacked Organic/inorganic Vapor Barrier Structure Encapsulated Flexible Plastic Substrates Prepared using Plasma-enhanced Chemical Vapor Deposition," *Extended Abstracts of the 2010 International Conference on Solid State Devices and Materials*, 2010, pp. 495-496, Tokyo, Japan.

Komolprasert, V., "Food Packaging: New Technology," *Handbook of Food Science, Technology, and Engineering*, Division of Food Processing and Packaging, U.S. Food and Drug Administration, Date unknown, Chapter 130, pp. 130-1 to 130-10, vol. 3.

Korner, L., "Diffusion Barrier Coatings for Polymer Containers Processed by Plasma Enhanced Chemical Vapor Deposition," A dissertation submitted to ETH Zurich for the degree of Doctor of Sciences, Diss. ETH No. 19023, 2010, one hundred seventy-seven pages.

Krstulovic, N. et al., "An Optical-Emission-Spectroscopy Characterizatoin of Oxygen Plasma During the Oxidatoin of Aluminium Foils," *Materials and Technology*, 2009, pp. 245-249, vol. 5.

Nakamura, S. et al., "Diffusion Coefficients of Disperse Dye to PE and PET Films in Supercritical Carbon Dioxide," Date unknown, six pages, Kanazawa University, Japan.

Nesheva, D. et al., "Raman Scattering and Photoluminescence from Si Nanoparticles in Annealed SiO$_x$ Thin Films," *Journal of Applied Physics*, Oct. 15, 2002, pp. 4678-4683, vol. 92, No. 8.

nGimat, "Welcome to nGimat: Barrier Coatings," 2008, two pages. [Online] [Retrieved on Feb. 28, 2011] Retrieved from the Internet<URL:www.ngimat.com/barrier/barriercoatings.html>.

Papakonstantinou, D.D. et al., "Etch Rate Measurement of Polyethylene Terephthalate Films Treated in Helium and Helium-Oxygen RF Discharges," *Proceedings of the 16th International Symposium on Plasma Chemistry (ISPC)*, 2003, six pages, Taormina, Italy.

PCT International Search Report and Written Opinion, PCT Application No. PCT/US2012/028660, dated Jun. 8, 2012, eleven pages.

Srivatsa, K. et al., "Optical Thin Films of Silica and Titania Deposited by Plasma Polymerisation Process: System Design and Fabrication," *Indian Journal of Engineering & Materials Sciences*, Jun. 2008, pp. 265-274, vol. 15.

Steves, S. et al., "Silicon Oxide Permeation Barrier Coating of PET Bottles and Foils Deposited by Hexamethyldisiloxan-oxygen Plasmas," *Institute for Electrical Engineering and Plasma Technology*, Date unknown, Ruhr-University Bochum, Bochum.

Van Hest, M., "High Rate Plasma Deposition of Silicon Oxide Like Films," 2002, one hundred eighty-two pages.

European Patent Office, Supplementary Search Report and Opinion, European Patent Application No. 12755370.9, dated Sep. 23, 2015, seven pages.

* cited by examiner

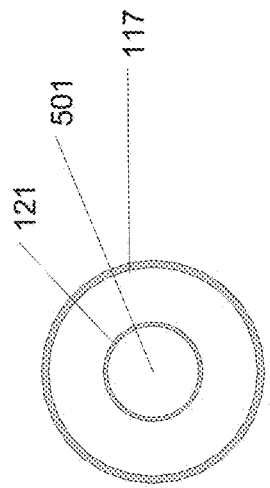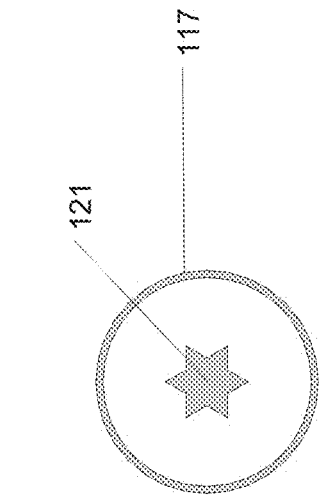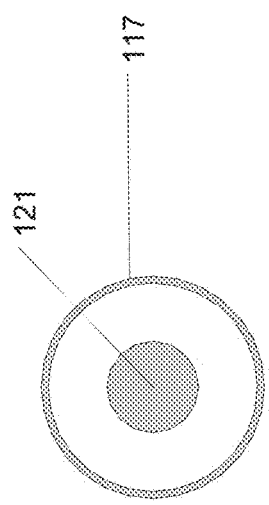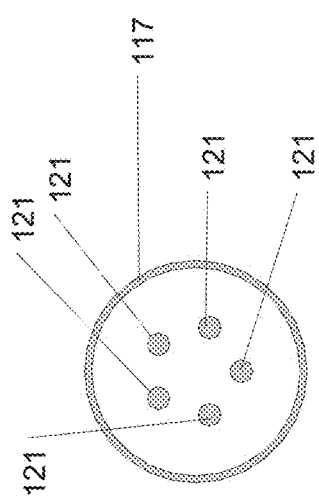

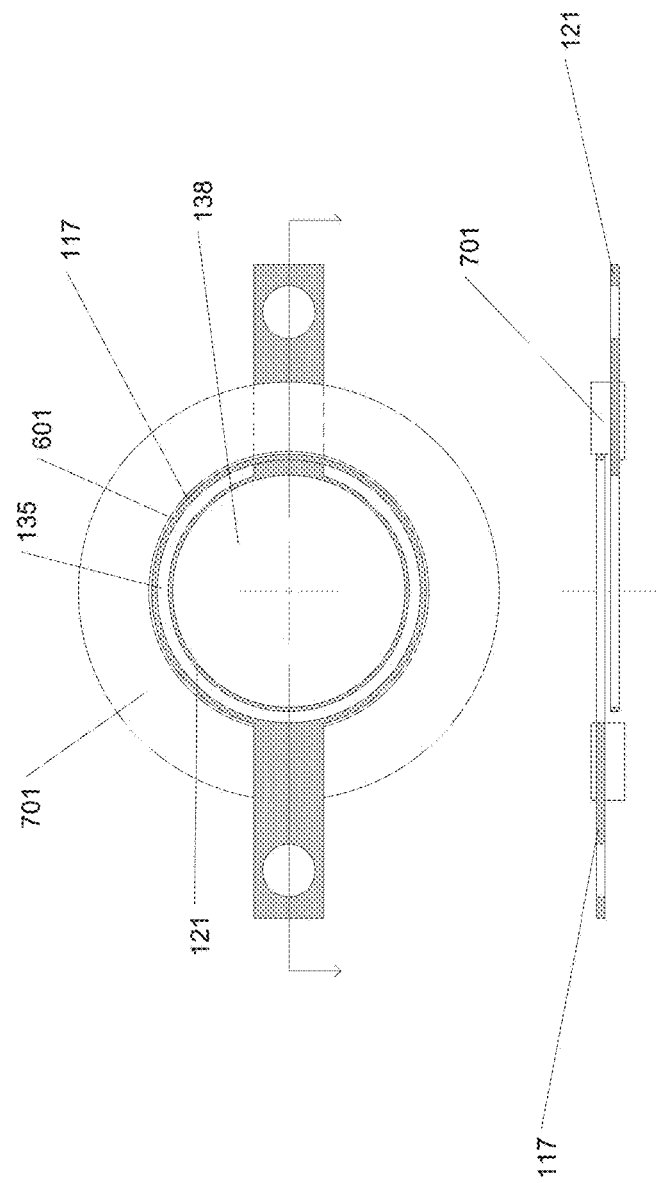

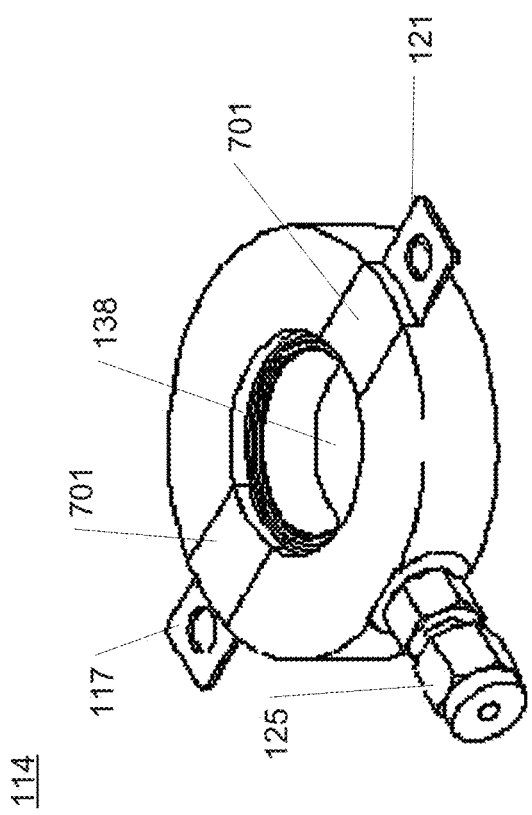

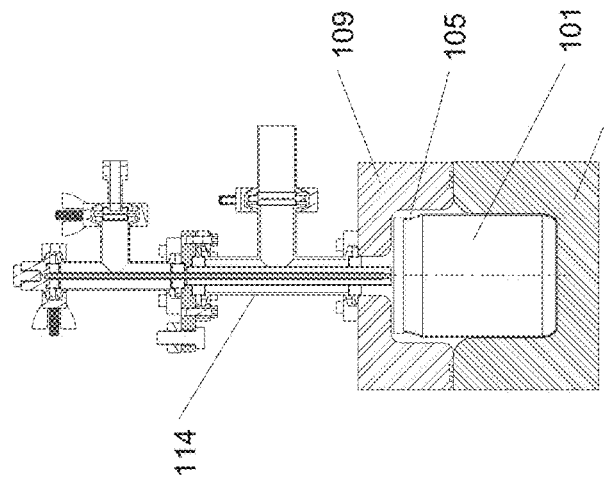
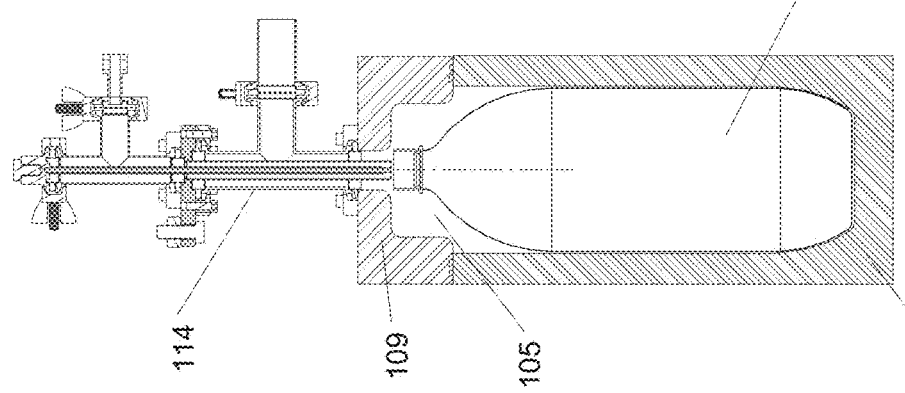
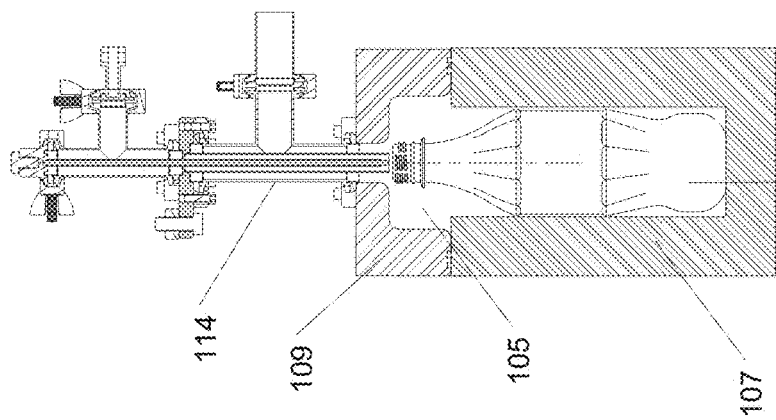

METHOD AND APPARATUS FOR TREATING CONTAINERS

RELATED APPLICATIONS

This application claims priority to U.S. Provisional Application 61/451,578 filed Mar. 10, 2011 which is hereby incorporated by reference in its entirety for all purposes.

FIELD

The disclosure relates to methods and apparatus for the treating of containers for sterilization or application of thin film linings.

BACKGROUND

The packaging industry utilizes plastic and metal containers for packaging of food and beverage products, pharmaceuticals, nutritional supplements, medical devices, supplies, containment vessels, household products, auto lubricants, and other products. These plastic and metal containers can have weak properties that limit their use and usable lifecycle.

For example, the shelf life of a product may depend on several properties including: oxygen, carbon dioxide, and water vapor transmission rates through the packaging container as well as chemical reactivity between the packaging and its contents. Glass ("$SiO_x$") is considered the benchmark material for providing content integrity. However, producing glass containers is costly, uses large energy resources, requires sterilization, and is cumbersome in handling and shipping due to the fragile nature and weight of glass. Recently, solutions have been introduced that use plasma energy to deposit a very thin $SiO_x$ film on the interior of plastic containers to obtain the barrier properties that address weaknesses in conventional plastic containers.

Other barrier films have also been developed such as diamond-like carbon and silicon oxynitride which can also improve performance. These solutions have gained some market acceptance; however, the cost of the capital equipment, size and complexity of the machines, lack of versatility, and overall cost of ownership to run the machines provide significant barriers to entry to most packaging companies and end-users of the containers.

Existing plasma deposition systems utilize one electrode in the container and one outside. This however limits the range of container geometries that can be treated by the apparatus and adapting the apparatus is expensive and difficult because the electrode configuration depends on the geometry of the container being treated.

Additionally, systems and processes exist to treat container surfaces for other reasons, such as, sterilization, surface texturizing, creating hydrophobic or hydrophilic properties, screen printing adhesion of inks, and others. Such treatments are required in many of the industries and applications noted above.

Further, metal containers such as tin, steel, and aluminum require coatings that may contain volatile solvents that are bad for the environment and/or BPA (bisphenol A) which has been shown by the FDA (food and drug administration) to interfere with natural hormone production and balance resulting in a FDA report in 2010 highlighting concerns of BPA exposure in fetuses, infants, and young children. The method and apparatus disclosed in this specification can also treat metal containers to provide solutions that replace the coatings currently in use.

For at least these reasons, there is a need to develop equipment and processes to overcome the challenges of the existing solutions while providing for the application of barrier films or other treatments on the interior of containers.

SUMMARY

A method of treating containers using radio frequency energy to disassociate chemical precursors which recombine depositing a film on surfaces near the reaction or treating the surfaces of the container (e.g., sterilization, texturizing, etc.). A chamber has been developed that integrates a method to deliver chemical precursors into the chamber volume, a mechanism to exhaust the chamber volume, an electrode assembly to disassociate the chemical precursors and produce a chemical reaction by which a film is deposited on the interior surface of the container, or the interior surfaces of the container are treated in aforementioned manner. In one embodiment, a production system utilizes a plurality of these chambers.

BRIEF DESCRIPTION OF THE DRAWINGS

The disclosed embodiments have other advantages and features which will be more readily apparent from the detailed description, the appended claims, and the accompanying figures (or drawings). A brief introduction of the figures is below.

FIGS. 5A-5D illustrates variations in the configuration of the inner electrode.

FIG. 7 illustrates one embodiment for optimization of an electrode assembly.

FIGS. 8A-C illustrates one embodiment for optimization of an electrode assembly.

FIGS. 13A-C illustrate additional shapes and volumes of containers that can be used with the system and method.

DETAILED DESCRIPTION

The figures and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Reference will now be made in detail to several embodiments, examples of which are illustrated in the accompanying figures. The figures depict embodiments of the disclosed system (or method) for purposes of illustration only. One skilled in the art will readily recognize from the following description that alternative embodiments of the structures and methods illustrated herein may be employed without departing from the principles described herein.

Figure 1:
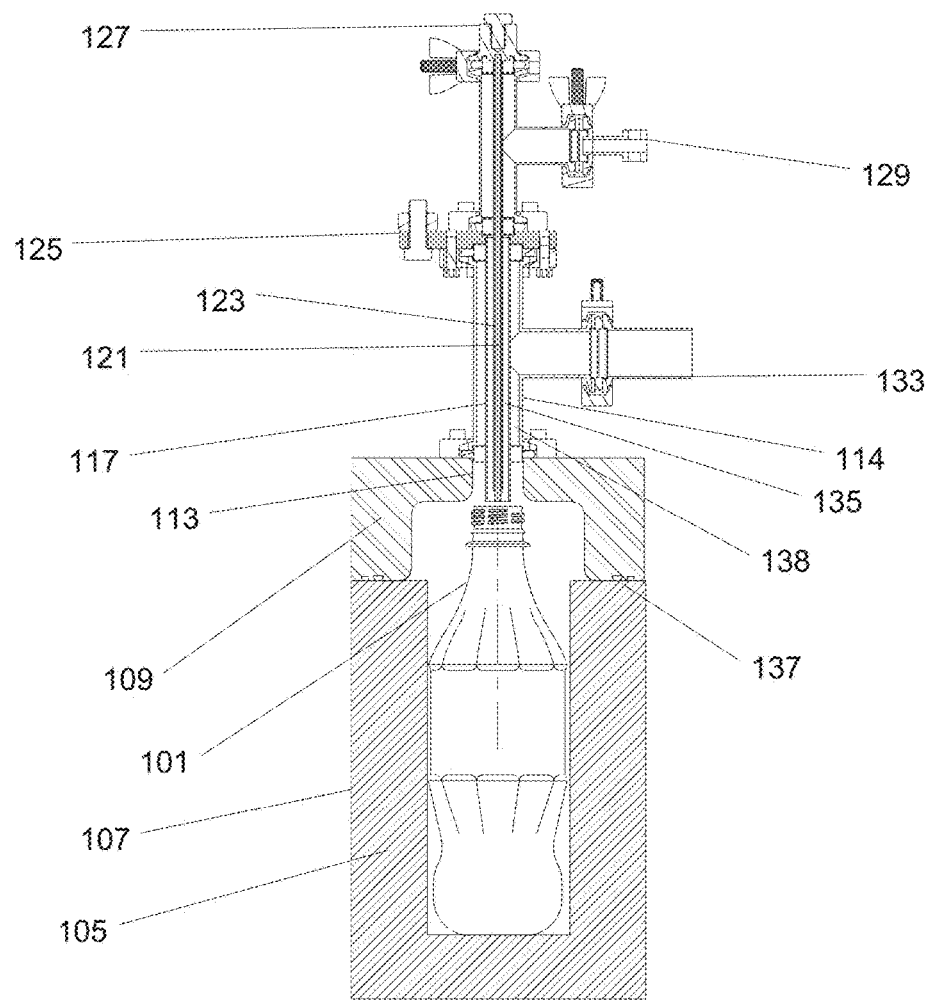
FIG. 1 illustrates one embodiment of a chamber design used to treat or deposit a film on surfaces of a container.

FIG. 1 illustrates apparatus for treating a container 101 according to one embodiment. The illustrated components include a chamber 105 having a lower housing 107, a gasket 137 and an upper housing 109 having an opening 113; an electrode assembly housing 114; an outer electrode 117; an inner electrode 121 surrounded by a dielectric sheath 123; an annulus 135; an exhaust escapement 138; an exhaust outlet 133; a precursor inlet 129; a cathode 127 and an anode 125.

The chamber 105 is configured to hold a container 101. The chamber 105 is formed by the lower housing 107 and the upper housing 109. The lower housing 107 and upper housing 109 are sealed using the gasket 137. The gasket 137 is sufficient to allow the maintenance of a vacuum or low pressure (sub-atmospheric pressure or alternatively about 5 Torr or less or between 5 mTorr to about 5 Torr) in the chamber 105. The upper housing 109 includes at least one opening 113 coupled to the electrode assembly housing 114 traversing the upper housing 109. The outer electrode 117 and the inner electrode 121 are disposed in the electrode assembly housing 114 in addition to the annulus 135 and the exhaust escapement 138. The outer electrode 117 is coupled to the anode 125 and the inner electrode 121 is coupled to the cathode 127. The electrodes 117 and 121 are arranged coaxially and the space between the outer electrode 117 and the inner electrode 121 forms the annulus 135 which is coupled to the precursor inlet 129. The area between the outer electrode 117 and the electrode assembly housing 114 forms the exhaust escapement 138 which is coupled to the exhaust outlet 133. The electrode assembly housing 114 also includes the exhaust outlet 133 and the precursor inlet 129.

In one embodiment, the lower housing 107 is metallic. Alternatively, the lower housing 107 is plastic with a conductive encasement to provide RF shielding to the surrounding environment. Any structurally stable machinable plastic can be used. Examples include, but are not limited to, delrin, acetel and nylon. The chamber 105 is enclosed by the upper housing 109. The upper housing 109 is made of an electrically conductive material such as, for example, but without limitation, aluminum or copper. The annulus 135 is the means through which precursor materials are provided for the creation of plasma.

In one embodiment the electrodes 117 and 121 are RF electrodes. The electrodes 117 and 121 are the means through which power is applied to precursor materials forming plasma. The electrodes 117 and 121 can be any electrically conductive material such as for example, copper. Plated metals are also possible and reduce erosion over time. The inner electrode 121 is surrounded by a dielectric sheath 123. Example materials for the dielectric sheath 123 include PVC, alumina ($Al_2O_3$) and zirconium oxide ($ZrO_2$). Voltage is applied to the electrodes 117 and 121 via the anode 125 and cathode 127. It is understood that for use with alternating current (AC), the designation of anode 125 as an anode and cathode 127 as a cathode are not fixed.

The precursor inlet 129 allows for introduction of precursor materials into the chamber 105 via the annulus 135. The exhaust escapement 138 is the means by which gasses leave the chamber 105 and the chamber 105 is evacuated via the exhaust outlet 133.

Figure 2:
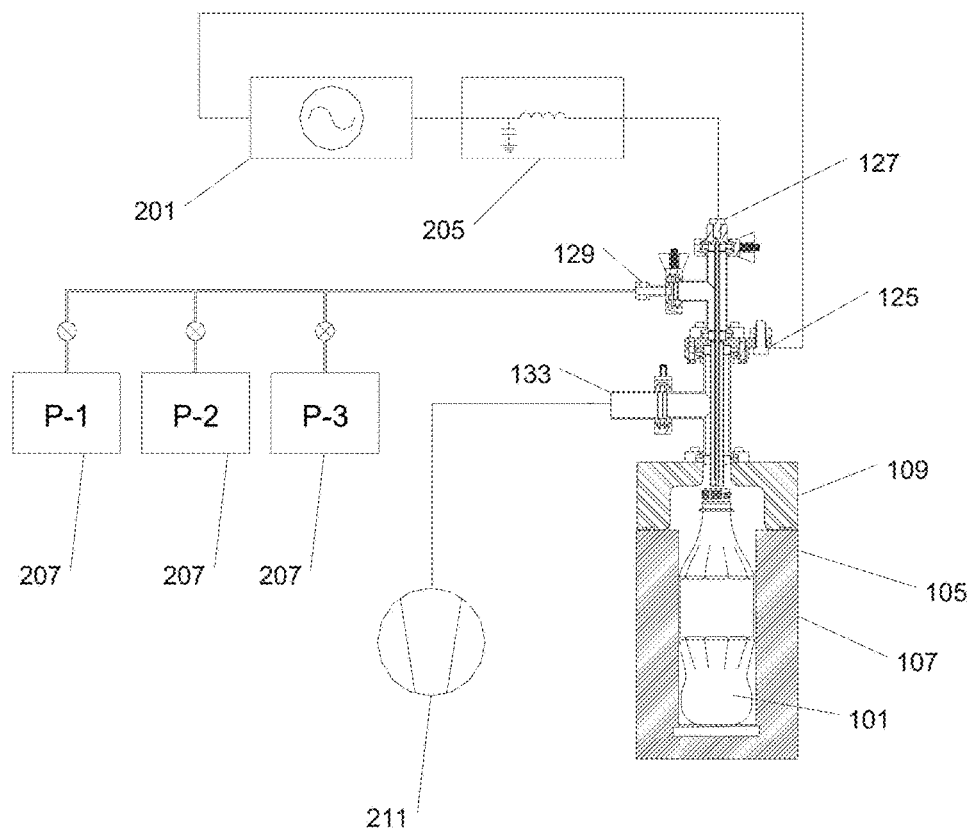
FIG. 2 illustrates the environment around the apparatus according to one embodiment.

FIG. 2 illustrates the environment around the apparatus according to one embodiment. The environment includes the chamber 105 having the upper housing 109 and lower housing 107; the precursor inlet 129; the exhaust outlet 133; the cathode 127; the anode 125; an alternating current (AC) power generator 201; a matching network 205; precursor sources 207 and a vacuum pump 211. The cathode 127 and anode 125 are configured to be coupled via a vacuum compatible coupling to connect to the AC power generator 201 and the matching network 205. The precursor inlet 129 is configured to be coupled via a vacuum compatible coupling to the precursor sources 207. The exhaust outlet 133 is configured to be coupled via a vacuum compatible coupling to the vacuum pump 211.

Typically, the AC power generator 201 is designed to operate with a 50Ω resistance (industry standard). A range of resistance is possible however. In an alternative embodiment, a direct current (DC) power generator is used. The matching network 205 is incorporated to transform the resistive and capacitive properties of the plasma to 50Ω to match that of the AC power generator's 201 impedance.

The example in FIG. 2 illustrates three precursor sources 207. In other embodiments, fewer or more precursor sources are possible. For the application of barrier films for containers, precursors include a silicon source (such as, but not limited to: silane gas ($SiH_4$), hexamethyldisiloxane HMDSO, tris[dimethylamino]silane TDMAS, tetramethoxysilane TMOS, triethoxysilane, or tetraethyloxysilane (TEOS) and oxygen gas ($O_2$) to form silicon oxide ($SiO_x$)). To form silicon oxynitride ($SiO_xNy$) films, a third precursor, nitrogen gas ($N_2$) is added. For the application of aluminum containing films to containers, precursors include an aluminum source such as an aluminum alkoxide, trimethylaluminum (TMA) or $AlCl_3$. Additional precursors could be implemented to form other films, provide dopants to tailor the film properties (such as, but not limited to: I/R or U/V filtering), provide a diluent gas, provide pretreatments to prepare the container surface, or sterilize the container. He, $N_2$ and Ar are useful as carriers for other precursor materials. Ar is also useful for initial plasma creation.

For the application of sterilization, example precursors include $O_2$, $N_2$, and nitrous oxide ($N_2O$). When oxygen is used as a precursor, the resulting atomic oxygen and ozone sterilizes the container 101. Sterilization is advantageous in many industry uses where organic contamination is of concern, including but not limited to: food & beverage, medical, petroleum, and general containment. For this reason, it is reasonable to expect sterilization can be an advantageous initial step in multistep treatments and deposition.

The vacuum pump 211 is the means by which the chamber 105 is evacuated and may be a single pump or a combination of pumps. In one embodiment, the chamber 105 is evacuated from atmospheric pressure to less than 5 Torr. In one embodiment the vacuum pump 211 is capable of evacuating 10 liters from ATM to 0.5 Torr in ≤5 seconds. Examples of vacuum pump 211 usable with the disclosed system include those from B.O.C. Edwards in Sanborn, N.Y.; Oerlikon Leybold Vacuum of Cologne, Germany; Kashiyama-USA in Fremont, Calif.; Toyoda Machinery USA in Arlington Heights, Ill.; and Ebara Technologies, Inc. of Sacramento, Calif.

Figure 3:
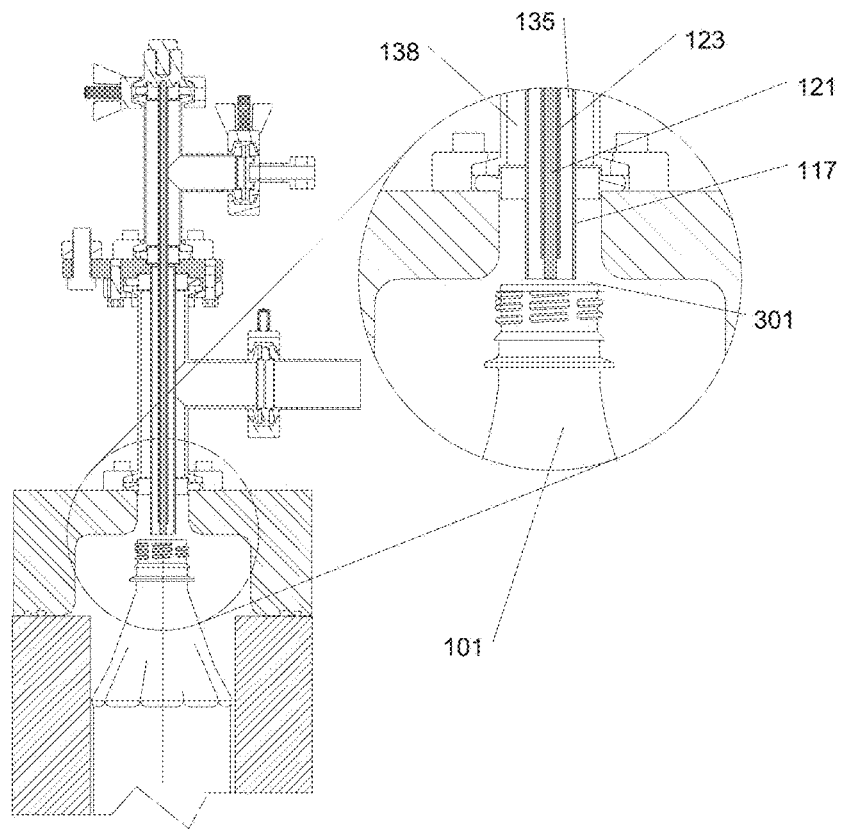
FIG. 3 illustrates the configuration of the electrodes in greater detail.

FIG. 3 illustrates the configuration of the electrodes 117 and 121 in greater detail. FIG. 3 includes the inner electrode 121 with dielectric sheath 123, the outer electrode 117, annulus 135, the exhaust escapement 138 and the container 101. The outer electrode has a larger diameter than the inner electrode and the coaxial arrangement of the electrodes 117 and 121 is particularly efficient for forming plasma from the precursor materials. In one embodiment, the inner electrode 121 has a diameter of at least ⅛ in. and the dielectric sheath 123 ends ⅛-1" from the end of the inner electrode 121 leaving the last portion of the inner electrode 121 unshielded. The portion of the inner electrode 121 that is unshielded is where plasma is formed and thus the amount of unshielded inner electrode 121 determines where plasma formation starts in operation. In one embodiment, the outer electrode 117 is sized to provide inertial flow of the precursor into the chamber cavity so that the mass flow of precursor materials can be efficiently disassociated by RF power delivered to the electrodes. For example, if the inner electrode has a diameter of about ⅛ inch, the outer electrode may have an inner diameter of ¼ to ½ in. Alternatively, because creation of plasma for disassociating the precursor materials depends on the relationship between the power input, the chemical species, the process pressure, and the chemical flow rate, and the sizes of the inner electrode and outer electrodes; the sizes of the electrodes can vary significantly. The electrodes 117 and 121 are configured to end right before the opening of the container 101 to be treated when the container 101 is inserted into the chamber 105 to be treated. In this embodiment, the area 301 between the top of an inserted container 101 and the end of the electrodes 117 and 121 is 5-10 mm for containers 101 with wider openings. The electrodes 117 and 121 can also be configured to extend down into an inserted container 101. This is useful for containers 101 with openings less than 38 mm in width.

Figure 4A:
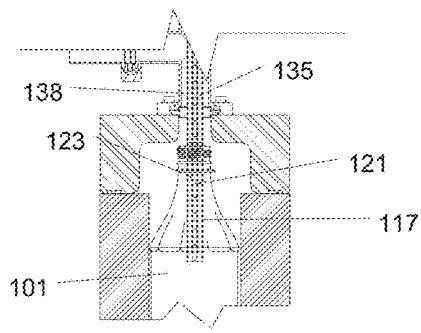
FIGS. 4A-D illustrates alternative embodiments of electrode configurations.
Figure 4B:
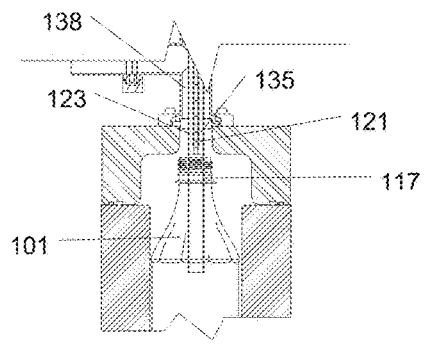
Figure 4C:
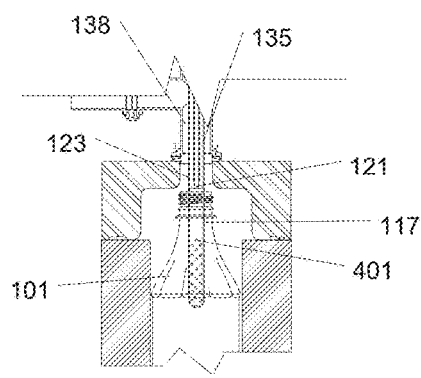

FIGS. 4A-D illustrate alternative electrode configurations. Alternative configurations improve and optimize deposition uniformity on various container geometries. Each configuration illustrates the container 101, the inner electrode 121 with dielectric sheath 123, the outer electrode 117, the annulus 135 and the exhaust escapement 138. Both electrodes 117 and 121 can be configured to extend into the chamber 101 as shown in FIG. 4A. The electrodes 117 and 121 can be configured to extend as much as halfway or more into the height of the container 101. The distance that the electrodes 117 and 121 are configured to extend into the container 101 depends on the height of the container 101, diameter of the opening of the container 101 and internal diameter of the container 101. For example; the geometry shown in FIG. 3 may provide better deposition coverage for low aspect ratio containers where the diameter of the container mouth may be greater than 38 mm, while an extended probe as shown in FIGS. 4A-D may provide better uniformity on high aspect ratio containers and those with openings smaller than 38 mm. FIG. 4A illustrates the extension of the inner electrode 121 with dielectric sheath 123 and the extension of outer electrode 117 into the container 101 to increase uniformity of treatment chemistry on the interior walls of container 101 before the chemistry is exhausted through exhaust escapement 138. In another embodiment, simply extending the outer electrode 117 into the container may provide for efficient treatment of the container as shown in FIG. 4B.

Alternatively, the electrodes 117 and 121 differ in length from one another. The outer electrode 117 extends at least as far as the end of the dielectric sheath 123. In some cases it may be beneficial to extend the outer electrode 117 longer than the inner electrode 121. In this embodiment, the outer electrode 117 acts as a conduit of the plasma into the target container. In some embodiments, the outer electrode 117 incorporates openings 401, shown in FIG. 4C. This allows for more uniform deposition of a coating. Openings 401 typically range in effective cross-sectional area equivalent to hole sizes from 0.001" to 0.050" where the size is determined by the process pressure, the process flow rate, and chemical species delivered between the electrodes. In this configuration the end of the outer electrode is closed to force the chemical species through the openings 401.

Figure 4D:
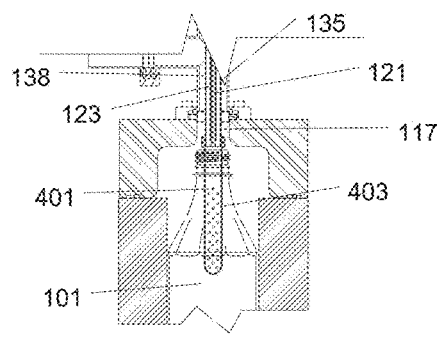

In yet another alternative, illustrated in FIG. 4D, the added uniformity of deposition is accomplished through the addition of a baffle 403 with openings 401 to the end of the outer electrode 117. The baffle 403 comprises a dielectric material similar to that used for the dielectric sheath 123 on the inner electrode 121.

Turning now to FIGS. 5A-5D, illustrated are variations in the configuration of the inner electrode 121. Varying the inner electrode 121 configuration can decrease power required to generate the plasma and/or delivering the active species. FIG. 5A illustrates a solid inner electrode 121. FIG. 5B illustrates a hollow cylindrical inner electrode which allows for precursor materials or other gasses to be introduced through the hollow center 501. FIG. 5C illustrates the inner electrode 121 as multiple inner electrodes 121 which operate as a single unit. FIG. 5D illustrates a shaped inner electrode 121. The points on the star-shape inner electrode 121 act as an antenna and discharge electrical charges collected at the points to the outer electrode 117.

Figure 6:
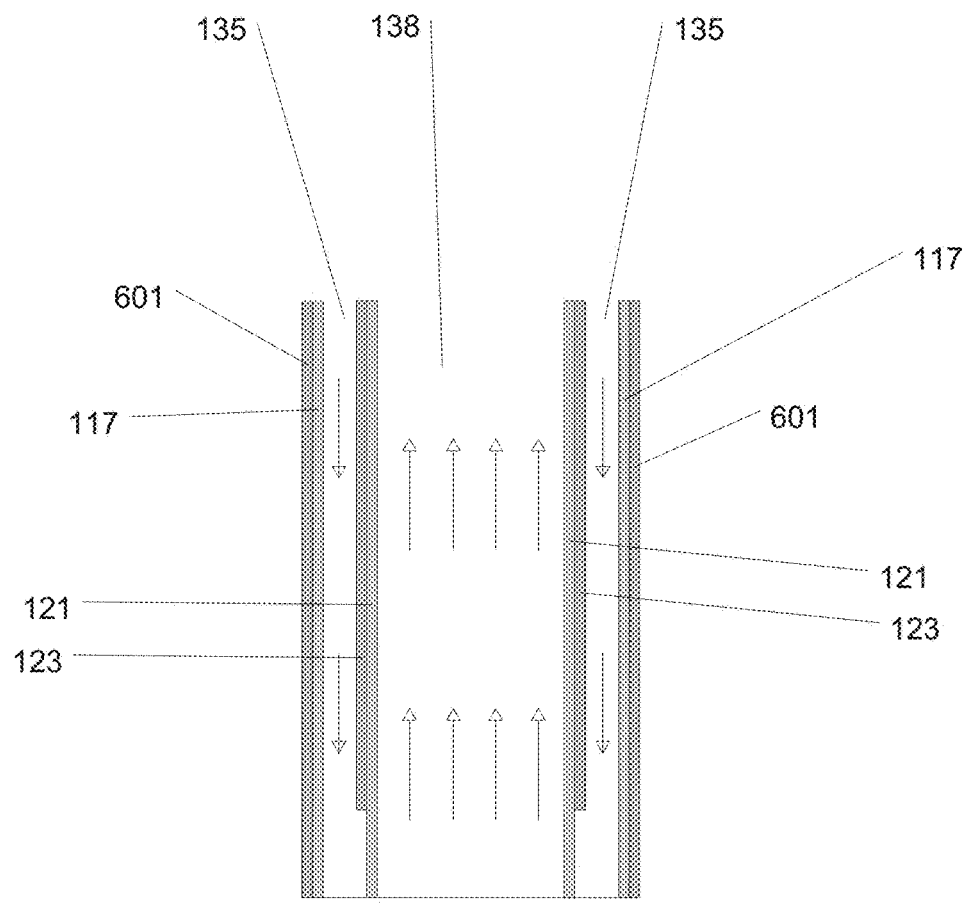
FIG. 6 is a general conceptual drawing that describes a hollow inner electrode configured as the conduit for gasses exiting the chamber.

An alternate co-axial assembly where the inner electrode 121 is hollow and its center is used as the exhaust escapement 138 is also possible and illustrated in FIG. 6. FIG. 6 is a general conceptual drawing that describes the principals in this configuration and includes the inner electrode 121 with dielectric sheath 123; the outer electrode 117 with a dielectric sheath 601; the annulus 135 and the exhaust escapement 138. The exhaust escapement 138 is configured to connect to the exhaust outlet 133. Precursor material enters the chamber in the annulus 135 between the outer electrode 117 and inner electrode 121. In this embodiment, the outer electrode 117 has a dielectric sheath 601. This eliminates grounding to other chamber components and further improves conductance to the vacuum pump and leads to more efficient deposition on wide mouth containers.

Referring now to FIG. 7, optimization of the electrode assembly according to one embodiment is illustrated. FIG. 7 includes the inner electrode 121; the outer electrode 117 with dielectric sheath 601; the annulus 135; exhaust escapement 138; and dielectric layers 701. The electrodes 117 and 121 are flat as opposed to cylinders and packaged with interchanging conductive and dielectric layers 701. This is beneficial as because it provides electrical insulation while reducing the materials required and providing for cost effective design and servicing. Precursor materials enter the chamber in the annulus 135 where it is disassociated and enters the chamber and is then exhausted through the exhaust escapement 138.

Figure 8B:
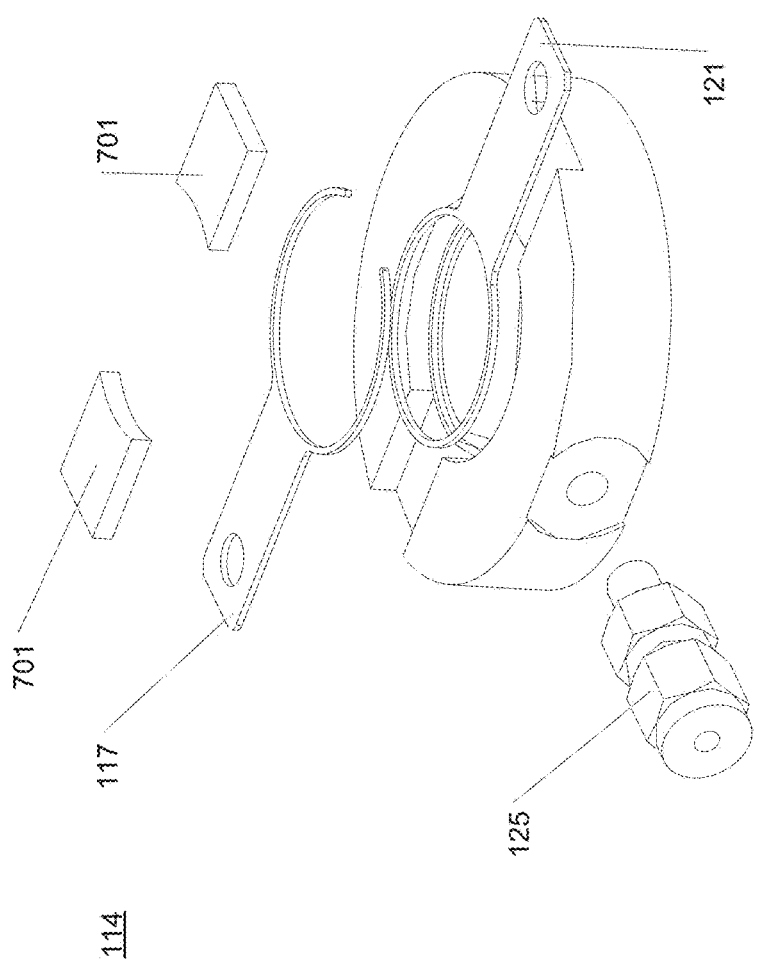
Figure 8C:
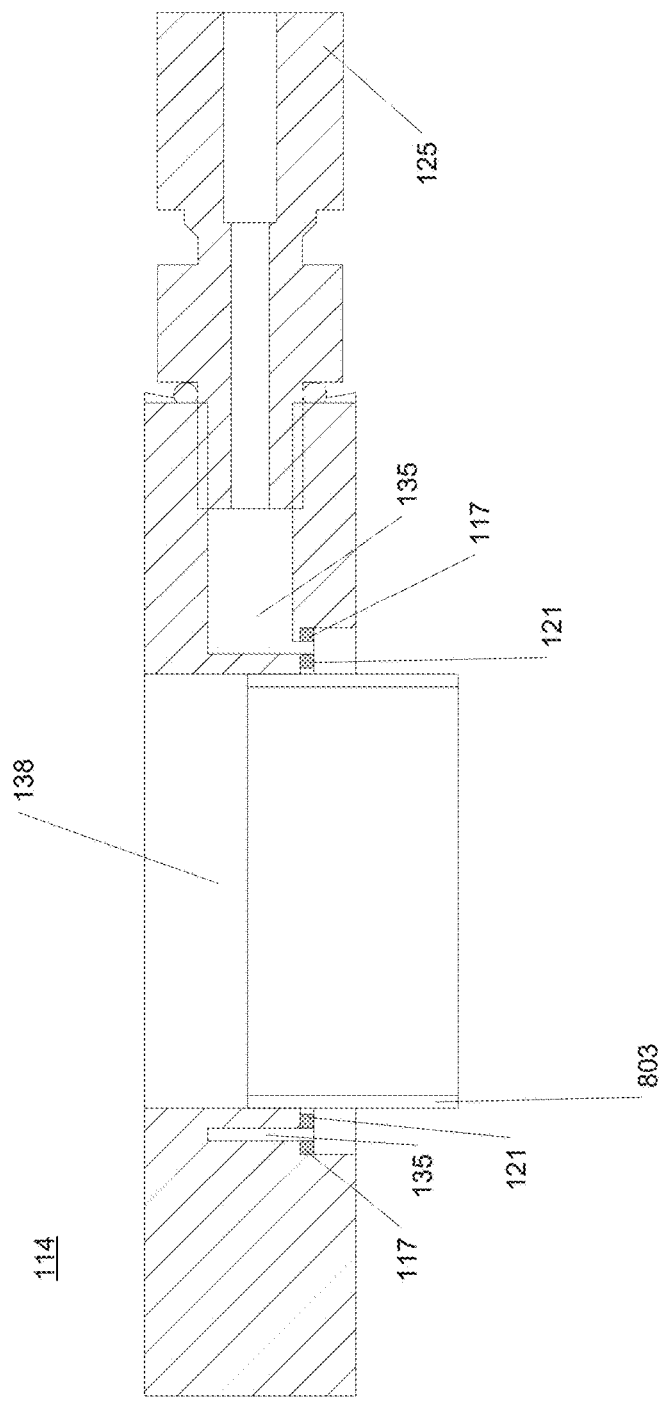

FIGS. 8A-C illustrate an alternate electrode assembly housing 114. All three figures illustrate the internal electrode 121; outer electrode 117; dielectric layers 701; exhaust escapement 138 and precursor inlet 129. Referring to FIG. 8A, the inner electrode 121 and the outer electrode 117 are layered with dielectric layers 701. The exhaust escapement is configured to connect to the exhaust outlet 133. The precursor inlet 129 for introduction of one or more precursor materials. FIG. 8B illustrates an exploded view of the electrode assembly housing 114 in FIG. 8A.

FIG. 8C illustrates a cross-sectional view of the electrode assembly housing 114 in FIG. 8A. FIG. 8C includes additional components: the annulus 135 and an exhaust baffle 803. The precursor inlet 129 is configured to be coupled to the annulus 135. The exhaust baffle 803 is configured to be coupled to the exhaust escapement 138.

The exhaust baffle 803 increases flow uniformity into the chamber before it is exhausted through the exhaust escapement and to the exhaust outlet 133. This provides the benefit of the precursor materials to flow around and above the electrodes 121 and 117.

Figure 9:
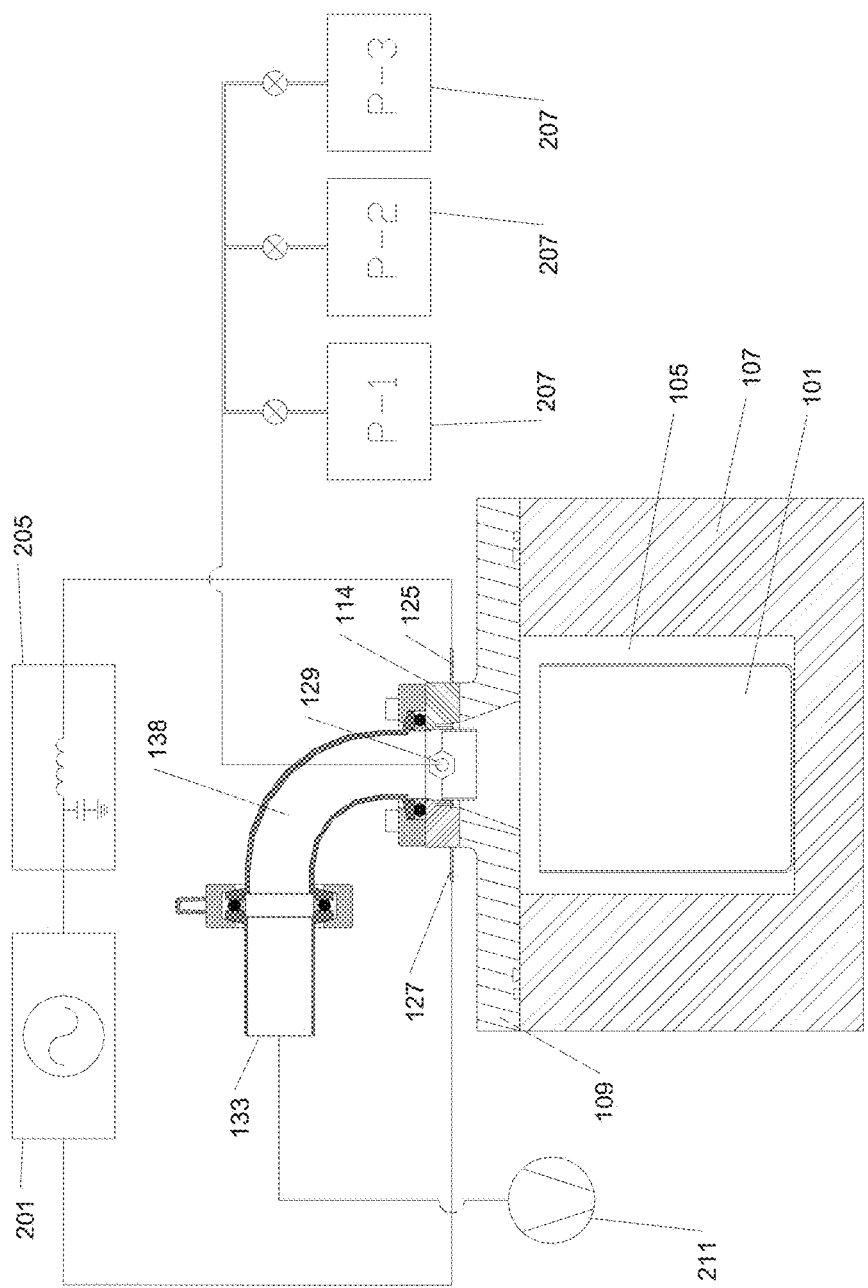
FIG. 9 illustrates an environment utilizing the flatter electrodes.

FIG. 9 illustrates an environment utilizing the alternate electrode assembly housing 114 illustrated in FIGS. 7-8. FIG. 9 includes the chamber 105 having the upper housing 109 and lower housing 107 and a container 101 disposed therein; the electrode assembly housing 114; the anode 125; the cathode 127; the precursor inlet 129; the precursor sources 207; the exhaust escapement 138; the exhaust outlet 133; the vacuum pump 211; the AC power generator 201 and the matching network 205. The cathode 127 and anode 125 are configured to be coupled via a vacuum compatible coupling to connect to the AC power generator 201 and the matching network 205. The precursor inlet 129 is configured to be coupled via a vacuum compatible coupling to the precursor sources 207. The exhaust outlet 133 is configured to be coupled via a vacuum compatible coupling to the vacuum pump 211.

Figure 10:
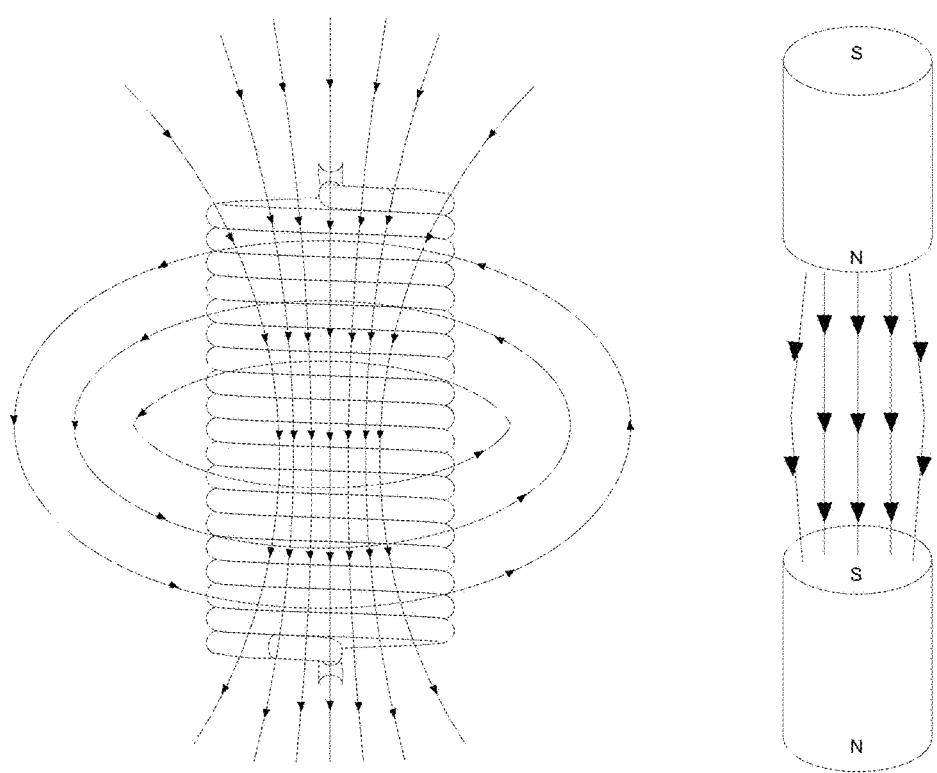
FIG. 10 illustrates example magnetic flux lines created in solenoids or permanent magnets.

FIG. 10 illustrates magnets or solenoids (electromagnets) to increase efficiency of transport of the active plasma species. Ions and radicals flow in helical paths along the flux lines created by the magnetic field, thus, confining the plasma, increasing plasma density. By providing such an environment, it is possible to direct deposition. This is done in a variety of ways depending on placement of permanent and electromagnets to address container aspect ratio and shape. FIG. 10 illustrates examples of magnetic flux lines created in solenoids or permanent magnets.

Figure 11:
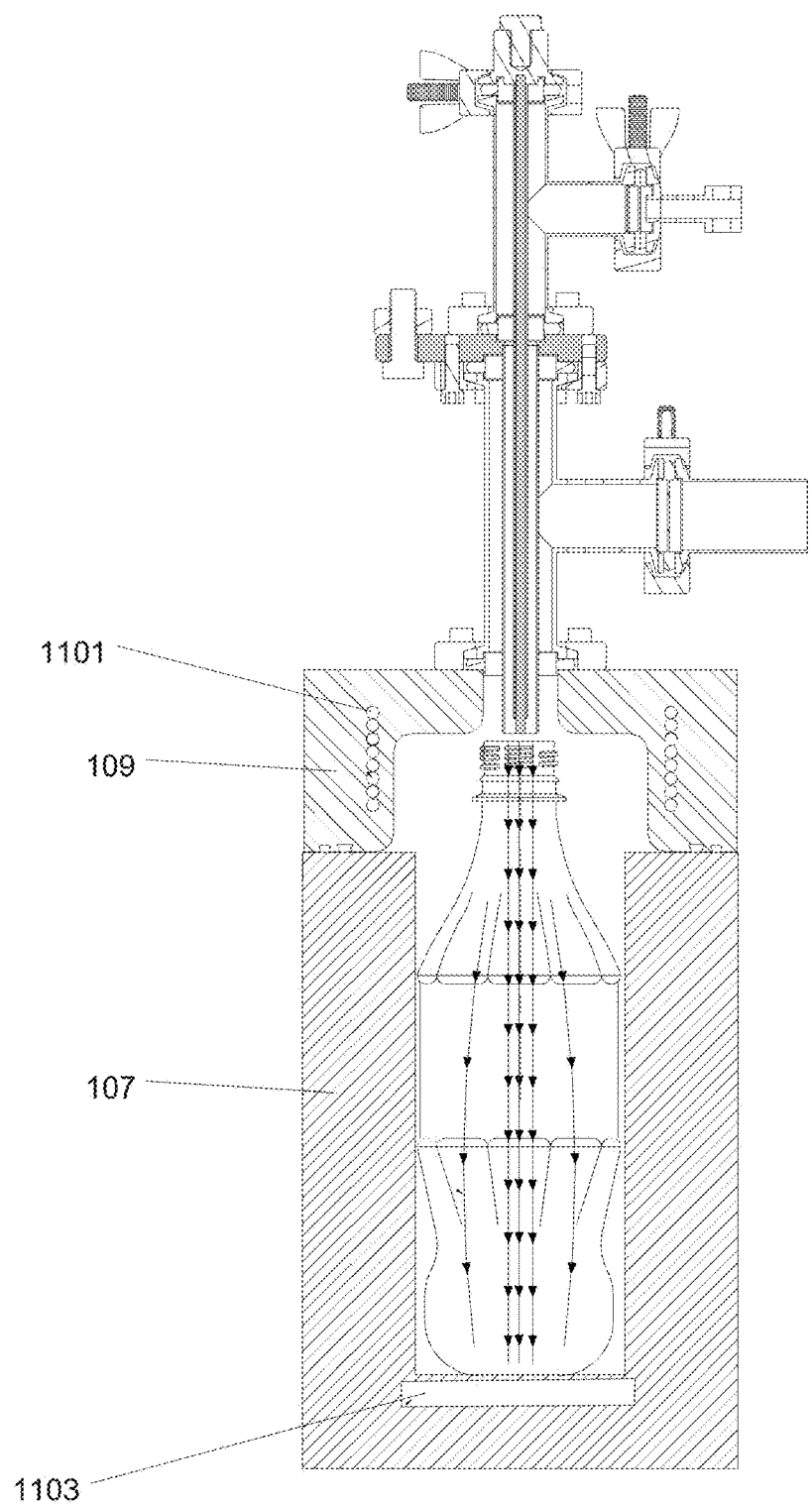
FIG. 11 illustrates one embodiment for use of magnets in the system.

FIG. 11 illustrates an electromagnet 1101 incorporated in the upper housing 109 to confine plasma into the narrow neck of the container and a magnet 1103 incorporated into the lower housing 107 to direct the flux lines to the base of the container. Magnets can also be incorporated in a variety of other ways to confine and direct the plasma to address the features of the container shape and volume.

Figure 12A:
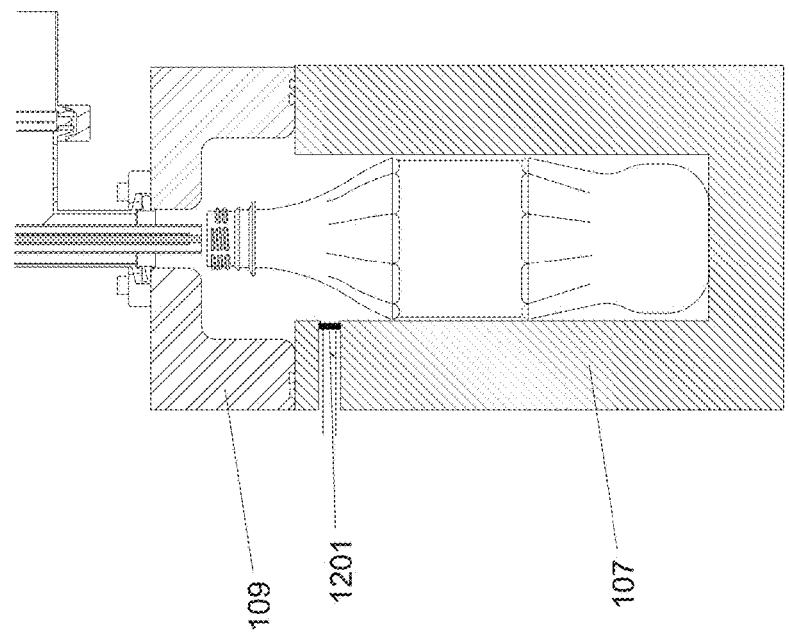
FIGS. 12A-B illustrate two example embodiments of incorporating a photodiode quality control feature.
Figure 12B:
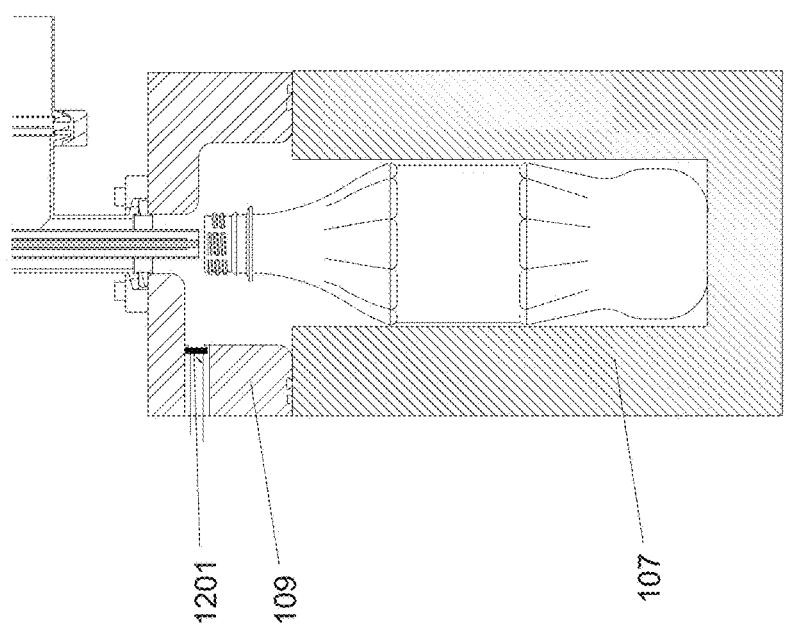

FIGS. 12A-B illustrate incorporation of an optional photodiode 1201 in the disclosed apparatus. In FIG. 12A, the photodiode 1201 is incorporated in the upper housing 109. In FIG. 12B, the photodiode 1201 is incorporated into the lower housing 107. Photodiodes 1201 are useful in production environments where quality control and process monitoring are important. The photodiode 1201 validates the presence and duration of plasma activation. Photodiodes 1201 are widely available in a variety of compact form factors and specific wavelength detection ranges. Photodiodes 1201 have response times that are very fast (e.g., <5 ms) for accurate time measurement. Different wavelengths are used depending on the treatment of the containers. Oxygen plasma fluoresces at 777 nm, nitrogen at 357 nm, $NO_2$ at 590 nm. Different photodiodes would be used to validate various process steps, $O_2$, $O_2+N_2$, $O_2$+silicon for example. The exact wavelengths targeted are determined by experimental observation at the optimized process (different mixtures of gases will move the peak luminescence).

FIGS. 13A-C illustrates the system used with a variety of container 101 shapes. Each of FIGS. 13A-C illustrate the container 101; chamber 105; upper housing 107 and lower housing 109. FIG. 13A illustrates a smaller bottle of about 0.5 L as the container 101 disposed within the chamber 105. FIG. 13B illustrates a larger bottle of about 1 L as the container 101 disposed within the chamber 105. FIG. 13C illustrates a jar as the container 101 disposed within the chamber 105. In the illustrated examples the lower housing 107 is different in each example to accommodate the different shaped containers 101. However, the upper housing 109 and electrode assembly housing 114 did not need to be modified. This is especially useful when using RF power for creating the plasma because RF power does not require a waveguide. If microwave plasma is used, a waveguide is constructed geometrically of the hardware leading from the energy source to the target container and takes the geometry of the container in account. Thus adapting a chamber to different containers when using microwave plasma requires significant changes to the hardware from the energy source. While FIG. 13 illustrates the different containers 101 that substantially fill the chamber 105, this is not essential. The disclosed method and apparatus operate as well when there is space between the container 101 and the walls of the chamber 105.

Figure 14:
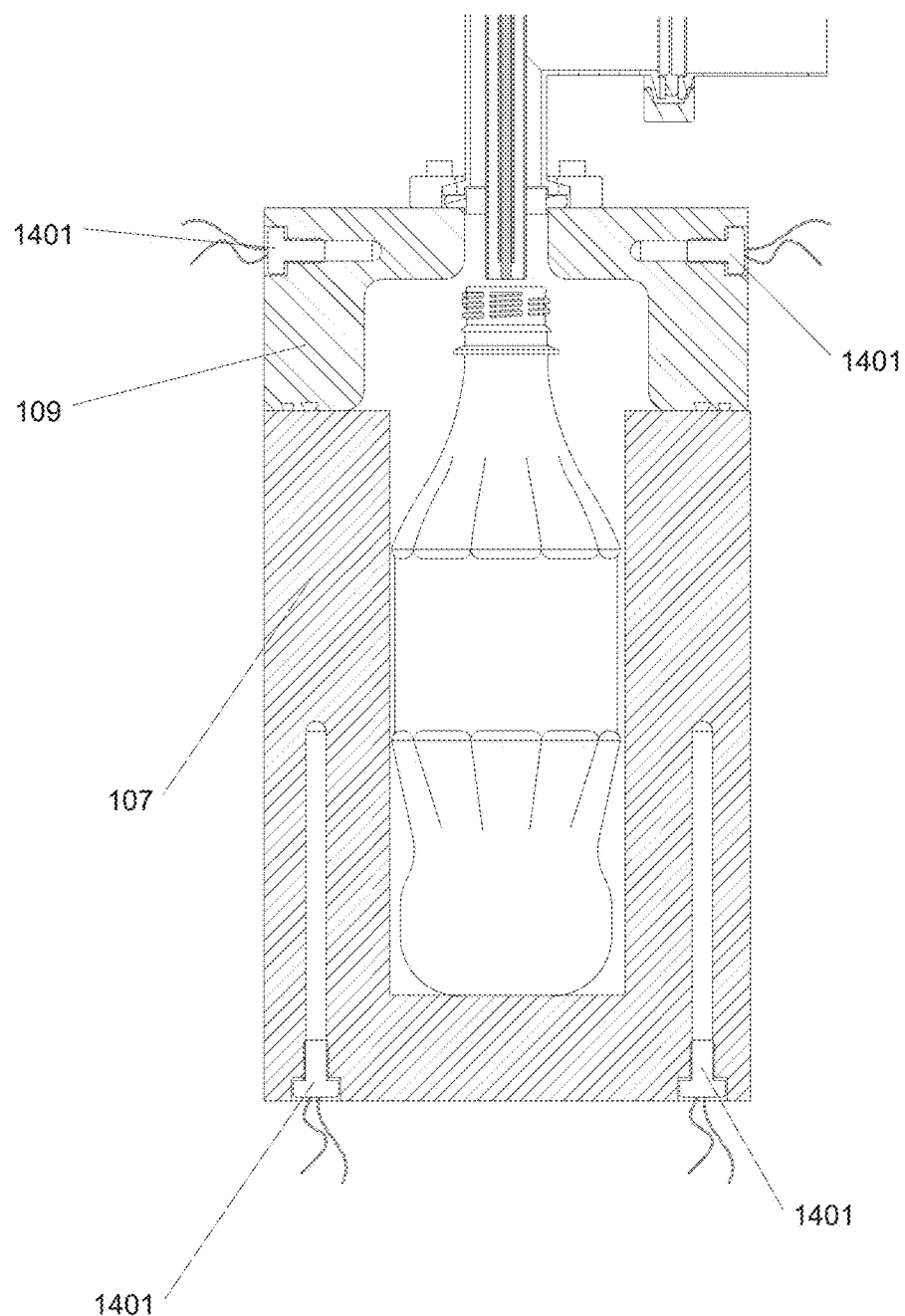
FIG. 14 illustrates heaters incorporated into the apparatus.

FIG. 14 illustrates heaters 1401 incorporated into the apparatus. FIG. 14 includes the upper housing 109; lower housing 107 and heaters 1401. Heaters 1401 are incorporated into the lower housing 107 and the upper housing 109. In alternative embodiments, one or more heaters 1401 are only incorporated into the lower housing 107 or the upper housing 109. Useful heaters 1401 include resistive type heaters activated by input of electrical energy. These are commonly known as fire-rods. Other methods and types of resistive heaters could be used to obtain the desired result. Use of heaters 1401 to heat the container 101 while treating is useful in avoiding film failure when the treatment of the container 101 comprises application of a film. The film failure occurs when the container 101 is placed in an environment of higher temperature. Film failure occurs due to the difference in growth between the container 101 and the film applied due to coefficient of thermal expansion having different values for different materials. Film failure occurs as delamination, fractures, or pinholes. Film failure is addressed by pre-heating the container 101 with the one or more heaters 1401, to a predetermined temperature, before and during the process of depositing the film.

The heating of the container 101 also results in the container 101 and the film entering a compressive state as the coated container cools. Thus when the coated container 101 is exposed at a later time to elevated temperatures, the container 101 does not experience the level of tensile stress that causes failure. Most materials are stronger in compressive stress than in tensile stress.

Figure 15:
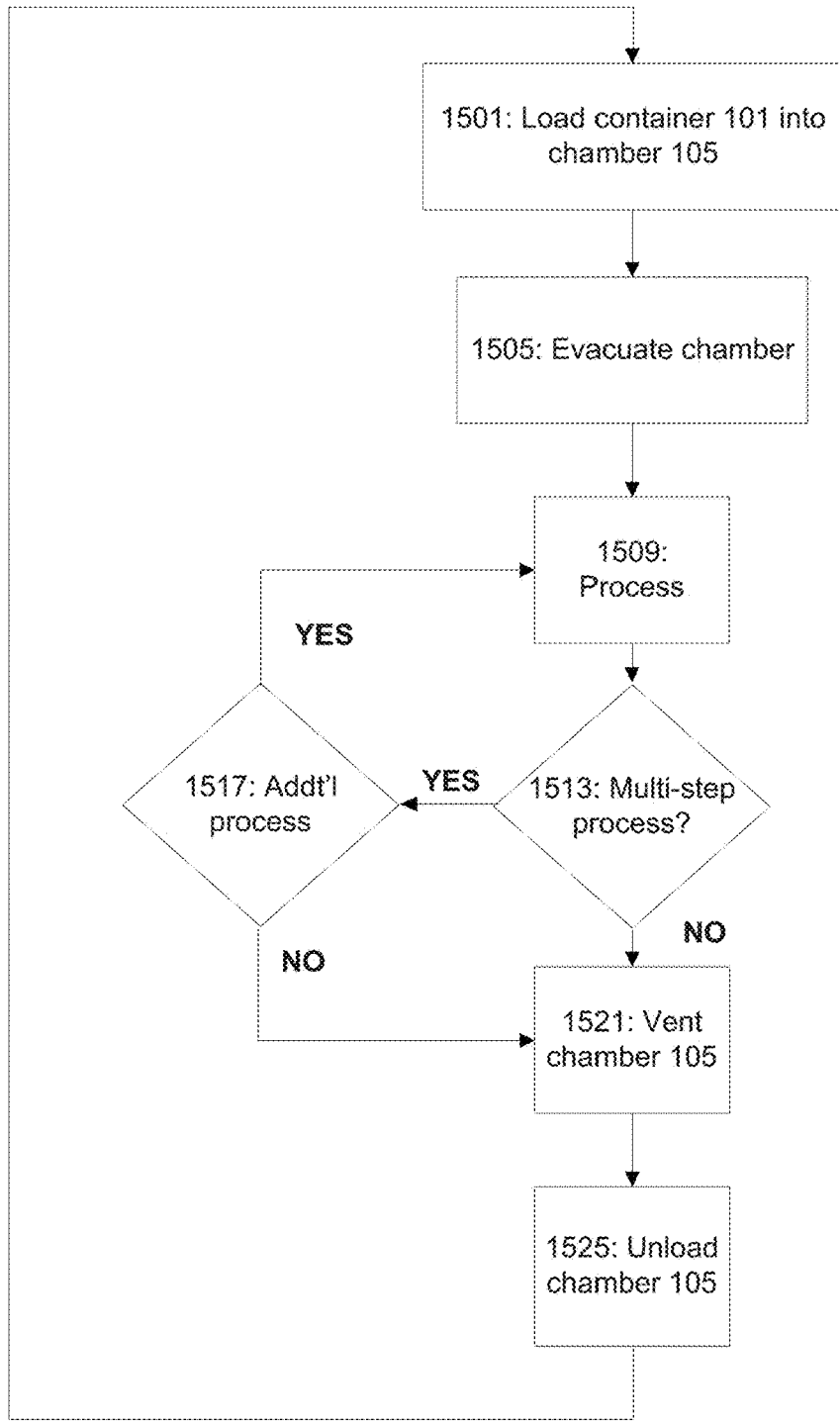
FIG. 15 illustrates a flow chart of one embodiment of a method for coating treating a container.

FIG. 15 is a flow chart illustrating the operation of the method. The process steps may be controlled manually or by automated means by implementing such instrumentation, times, relays, etc. that would be required for automated operation. The container 101 to be treated is loaded 1501 into the chamber 105. The upper housing 109 is closed. The chamber 105 is then evacuated 1505. The desired treatment process is then started 1509. The precursor materials for the process flow into the chamber 105 for a predetermined amount of time and the RF power started for a predetermined amount of time. Examples of applied RF power include 13.56 MHz and 400 kHz. The electrodes 117 and 121 are energized and the precursor gas or gasses enter the annulus 135. The gas is electrically excited by the energy and disassociates forming ions and radicals. The ions and radicals recombine as they collide with each other. For the formation of a film, for example, the collisions result in the formation compounds such as various $SiO_xN_y$, and physically deposit on the surfaces of the container 101, forming a thin layer of material on the interior surface of the container 101. Material is deposited for a predetermined time to create a conformal coating of predictive thickness. In one embodiment, the RF power remains in place for some time after the precursor materials have stopped flowing into the chamber 105. In operation, deposition rates can vary from fractions of nm/sec to multiple μm/sec depending on process pressure, power input, precursor flow, and precursor chemical concentration. In one embodiment, the system parameters are optimized to produce a film of 50-200 nm in less than 30 seconds for productivity reasons. In the case of $SiO_x$ films, publically published data has demonstrated effective barrier for oxygen and carbon dioxide at 50 nm. Alternately, a treatment that targets sterilization may target a process of less than 30 seconds to eliminate all biologicals present.

If the process is a multi-step process 1513, an additional process 1517 may be commenced by repeating step 1509 if the additional step requires additional gasses and plasma. An example of a multi-step process may begin with a precursor step to texturize the surface of a container to provide for better film adhesion, followed by a second precursor step to provide a film with good adhesion and compliance properties, followed by a third precursor step for an effective barrier film where the precursors of each step may be different from one another. Alternately, in some cases one step may involve treating a container with a precursor to sterilize the container. Further, a multi-step process may involve repeating deposition of the same film in a layered fashion. Another multiple step process could consist of a surface treatment followed by an in-situ deposition process such as an oxidation and clean of the depositing surface followed in-situ by a thin film deposition layer.

After processing is completed, the chamber 105 is vented 1521 bringing it back to atmospheric pressure. The container 101 is then unloaded 1525 from the chamber 105.

The described system and apparatus can be used with multiple chambers 105 in parallel allowing the treatment of multiple containers 101 at once. The apparatus can be reconfigured with different numbers of chambers 105 operating in parallel depending on the number of containers 101 to be treated at one time. Additionally, multiple chambers 105 can be configured for different shapes of containers 101. This may be accomplished by changing out the upper housing 109 or the lower housing 107 or both. In a machine with several chambers, the chambers are encased by a metallic enclosure to provide necessary RF shielding and safety or will have a metallized film or screen attached to the exterior for such requirements.

EXAMPLES

For all examples, the temperature of the chamber 105 is controlled by heater 1401. When treating plastic containers (comprising for example polyethylene terephthalate (PET)), the temperature of the chamber 105 is maintained at 70° C. or less. When treating metal containers (comprising for example aluminum, steel or tin), the temperature of the chamber 105 is maintained at less than 250° C. In all examples, the materials used include $SiH_4$, TEOS, HMDSO, $O_2$ and Ar.

Generally, for the various treating procedures, the chamber 105 is evacuated to between 50 mTorr and 5 Torr. The total flow rate of precursor materials to the chamber 105 is from 5 sccm to 500 sccm. The power applied to the electrodes 117 and 121 is from 10 W to 150 W. The time that power is applied forming plasma is from 5 ms to 60 seconds.

The method and apparatus is optimized for various families of container 101 geometries by numerical modeling, validated by experiments, based on various parameters and features which include, but are not limited to: container 101 distance to exhaust escapement 138, diameter of exhaust escapement 138, diameter of electrodes 117 and 121, deposition uniformity, deposition growth rate, particle formation and effluent.

Example 1 Oxidation and Cleaning of a Surface

The chamber 105 with the container 101 inserted is evacuated via the exhaust escapement 138 to a base pressure of 50 mTorr. Oxygen is flowed into the chamber 105 via the annulus 135 at 100 sccm. Plasma is created by applying 30 W power to the electrodes 117 and 121 for 5 seconds. When treating a plastic surface of a container 101, the result of this procedure is that the surface is cleaned. When treating metal surface of a container 101, such as Al, the result of this procedure is that the surface is treated and an inorganic oxide is grown such as $Al_2O_3$ in the case of an aluminum surface.

Example 2 Coating of a Surface with a SiO Film

The chamber 105 with the container 101 inserted is evacuated via the exhaust escapement 138 to a base pressure of 50 mTorr. HMDSO precursor vapor is carried to the chamber 105 via the annulus 135 using a flow of 10 sccm of argon which mixes with 50 sccm of oxygen prior to entering the chamber 105. The plasma is created by applying 30 W power to the electrodes 117 and 121 for 10 seconds resulting in a $SiO_x$ film of approximately 100 nm average thickness.

Example 3 Multi-Step Procedure

The procedure of Example 1 can be followed by the procedure in Example 2 to first clean and prepare a surface and then depositing a $SiO_x$ coating on the surface of the container 105.

The described apparatus is useful to treat containers by coating, texturizing and/or sterilizing them. The configuration of the electrodes together in an assembly is beneficial as the same assembly can be used to treat containers of various geometries. The plasma is formed at the electrodes and then disperses in the chamber and thus the configuration of the electrodes is not dependent upon the geometry of the container. This means that different geometry containers can be treated without significant changes to the partial pressure of precursor materials, concentration of precursor materials, the power applied or the time that the power is applied.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure. The language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

The invention claimed is:

1. An apparatus for treating a container comprising:
a chamber having an interior, a top portion and a bottom portion, wherein:
the top portion and the bottom portion are configured to fit together to close the chamber,
the top portion and the bottom portion are configured to provide vacuum-proof seal when the chamber is closed, the apparatus capable of maintaining a low pressure by the vacuum-proof seal and an evacuation means, and
the interior configured to hold the container to be treated;
a source of electrical power; and
an electrode assembly coupled to a chamber opening in one of the top portion or the bottom portion, the electrode assembly comprising:
an elongated electrode assembly housing having an outer diameter smaller than a diameter of the interior of the chamber,
a first electrode and a second electrode, wherein the first electrode is hollow and has a first diameter and the second electrode has a second diameter and the first diameter is larger than the second diameter, wherein the second electrode is a shaped electrode having a star-shape, wherein the first electrode and the second electrode are arranged coaxially relative to each other at least partially within the electrode assembly housing, and wherein the first and second electrodes are coupled to the source of electrical power so as to define a circuit and are positioned relative to each other such that electrical charges collected at points on the star-shaped second electrode discharge to the first electrode,
an annulus between the first and second electrodes, the annulus having a first cross-sectional opening with respect to the coaxial arrangement of the first and second electrodes through which treatment precursor materials are provided, and
an escapement configured to be coupled to a vacuum pump,
wherein:
the first and second electrodes associated with the circuit are at least partially located within the electrode assembly housing, and the electrode assembly housing is configured such that the first and second electrodes associated with the circuit extend into the container to be treated, and
the circuit defined by the first and second electrodes and the source of electrical power is configured to generate, at a plasma generation region, a plasma-forming voltage sufficient to generate plasma from the precursor materials flowing through the plasma generation region, wherein the plasma generation region:
is at least partially located within the annulus between the first and second electrodes; and
is at least partially shielded from one or more inner surfaces of the container to be treated, by the first electrode.

2. The apparatus of claim 1, wherein the first and second electrodes extend into the chamber.

3. The apparatus of claim 1, wherein the escapement is between the electrode assembly housing and the first electrode.

4. The apparatus of claim 1, wherein the second electrode has a first end closest to the interior of the chamber and the second electrode is coated with a dielectric material, and wherein the coating commences a predetermined distance from the first end and is applied to the second electrode in a direction away from the interior of the chamber.

5. The apparatus of claim 1, wherein the top portion comprises a metallic material.

6. The apparatus of claim 1, wherein the bottom portion comprises plastic having a conductive material encasement disposed thereon.

7. The apparatus of claim 1, wherein the low pressure falls within a pressure range of 5 mTorr to 5 Torr.

8. The apparatus of claim 1, wherein the first electrode and the second electrode are coupled to the source of electrical power comprising radio frequency (RF) power.

* * * * *